United States Patent
Mitani et al.

(10) Patent No.: US 9,128,026 B2
(45) Date of Patent: Sep. 8, 2015

(54) PARTICULATE MATTER PROCESSING APPARATUS

(75) Inventors: Shinichi Mitani, Susono (JP); Hiroshi Nomura, Gotenba (JP); Eiji Murase, Gotenba (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 1 day.

(21) Appl. No.: 13/519,021

(22) PCT Filed: Mar. 16, 2011

(86) PCT No.: PCT/JP2011/056300
§ 371 (c)(1),
(2), (4) Date: Jun. 25, 2012

(87) PCT Pub. No.: WO2012/124091
PCT Pub. Date: Sep. 20, 2012

(65) Prior Publication Data
US 2014/0007650 A1  Jan. 9, 2014

(51) Int. Cl.
G01N 15/00 (2006.01)
G01N 27/04 (2006.01)
B03C 3/41 (2006.01)
B03C 3/68 (2006.01)
F01N 11/00 (2006.01)
B03C 3/017 (2006.01)
G01N 15/06 (2006.01)

(52) U.S. Cl.
CPC .............. *G01N 27/04* (2013.01); *B03C 3/0175* (2013.01); *B03C 3/41* (2013.01); *B03C 3/68* (2013.01); *F01N 11/00* (2013.01); *F01N 11/007* (2013.01); *B03C 2201/24* (2013.01); *B03C 2201/30* (2013.01); *F01N 2560/05* (2013.01); *F01N 2560/12* (2013.01); *F01N 2900/1606* (2013.01); *G01N 15/0606* (2013.01); *Y02T 10/47* (2013.01)

(58) Field of Classification Search
CPC ............ G01N 27/407; G01N 15/0656; G01N 15/0606
USPC ................................... 73/23.31, 23.32, 31.07
See application file for complete search history.

(56) References Cited

U.S. PATENT DOCUMENTS 3,794,909 A * 2/1974 Smith .......................... 73/28.02
4,629,535 A * 12/1986 Oyama et al. .............. 205/784.5

FOREIGN PATENT DOCUMENTS

| JP | 2006-046281 A | 2/2006 |
| JP | 2006-105081 A | 4/2006 |
| JP | 2006-194116 A | 7/2006 |

*Primary Examiner* — Daniel S Larkin
*Assistant Examiner* — Alex Devito
(74) *Attorney, Agent, or Firm* — Sughrue Mion, PLLC

(57) ABSTRACT

An amount of aggregation of particulate matter is estimated with a high degree of accuracy. A particulate matter processing apparatus in which a processing part with an electrode installed therein is arranged in an exhaust passage of an internal combustion engine, wherein particulate matter is caused to aggregate by generating a potential difference between the electrode and the processing part, is provided with a power supply that is connected to the electrode and applies a voltage thereto, a current detection device that detects an electric current which passes through the electrode, an estimation device that estimates an amount of aggregation of the particulate matter based on the electric current detected at the time when the voltage is applied to the electrode, an air fuel ratio detection device that detects or estimates an air fuel ratio of an exhaust gas which flows through the exhaust passage, and a prohibition device which prohibits an estimation by the estimation device in the case of a rich air fuel ratio.

4 Claims, 2 Drawing Sheets

PARTICULATE MATTER PROCESSING APPARATUS

CROSS REFERENCE TO RELATED APPLICATIONS

This application is a National Stage of International Application No. PCT/JP2011/056300 filed Mar. 16, 2011, the contents of all of which are incorporated herein by reference in their entirety.

TECHNICAL FIELD

The present invention relates to a particulate matter processing apparatus.

BACKGROUND ART

There has been known a technique in which when an electric current passing through a discharge electrode is equal to or more than a predetermined value, it is determined that particulate matter (hereinafter also referred to as PM) has adhered to the discharge electrode, and an applied voltage to the electrode is caused to increase so as to remove the particulate matter from the discharge electrode (see, for example, a first patent document).

In addition, there has also been known another technique in which a discharge electrode is arranged in an exhaust passage of an internal combustion engine, and a corona discharge is caused to occur from the discharge electrode, whereby particulate matter is charged and condensed or aggregated (see, for example, a second patent document). By the condensation or aggregation of the particulate matter, the number of particles in the particulate matter can be decreased. Moreover, the diameters or sizes of particles in the particulate matter become large, so when a filter is arranged at a downstream side, it becomes easy to trap the particulate matter with the filter.

Here, there is a correlation between the electric current passing through the electrode, and the amount of particulate matter which has condensed or aggregated (i.e., this may also be the amount of decrease in the number of particles in the particulate matter). That is, the more the amount of aggregation of the particulate matter, the larger becomes the electric current passing through the electrode becomes. For this reason, the amount of aggregation of the particulate matter can be estimated from the electric current passing through the electrode. However, electricity flows through those substances other than the particulate matter which are contained in an exhaust gas. Accordingly, when the amount of aggregation of the particulate matter is estimated based on the electric current passing through the electrode, there will be a possibility that the accuracy of estimation may be made low due to the substances, other than the particulate matter, which are contained in the exhaust gas.

PRIOR ART REFERENCES

Patent Documents

First Patent Document: Japanese patent application laid-open No. 2006-105081
Second Patent Document: Japanese patent application laid-open No. 2006-194116

SUMMARY OF THE INVENTION

Problems to be Solved by the Invention

The present invention has been made in view of the problem as referred to above, and has for its object to estimate an amount of aggregation of particulate matter with a high degree of accuracy.

Means for Solving the Problems

In order to achieve the above-mentioned object, a particulate matter processing apparatus according to the present invention in which a processing part with an electrode installed therein is arranged in an exhaust passage of an internal combustion engine, wherein particulate matter is caused to aggregate by generating a potential difference between the electrode and the processing part, is provided with:

a power supply that is connected to said electrode and applies a voltage thereto;

a current detection device that detects an electric current which passes through said electrode;

an estimation device that estimates an amount of aggregation of the particulate matter based on the electric current detected by said current detection device at the time when the voltage is applied to said electrode by means of said power supply;

an air fuel ratio detection device that detects or estimates an air fuel ratio of an exhaust gas which flows through said exhaust passage; and a prohibition device that prohibits the estimation by said estimation device in cases where the air fuel ratio detected or estimated by said air fuel ratio detection device is a rich air fuel ratio.

Here, when a voltage is applied to the electrode, the particulate matter can be electrified or charged. The charged particulate matter is caused to move toward an inner wall of the processing part by means of a Coulomb force or a flow of the exhaust gas. The particulate matter, which has reached the inner wall of the processing part, releases electrons to the processing part, so electricity flows to a ground side rather than to the electrode. Then, the particulate matter, which has released the electrons, aggregates with other particulate matter which exists nearby, so it is possible to decrease the number of particles.

Then, the more the particulate matter aggregates, the larger the electric current passing through the electrode becomes, so the electric current detected by the current detection device becomes larger. That is, there is a correlation between the amount of aggregation of the particulate matter and the detected electric current, so the amount of aggregation of the particulate matter can be estimated based on the detected electric current. Then, if the amount of aggregation of the particulate matter can be estimated, the voltage to be applied can be controlled, for example, in such a manner that the aggregation of the particulate matter is facilitated. Here, note that when electrons are released from the particulate matter, an electric current is generated, and upon the release of the electrons, the particulate matter will aggregate, and hence, the amount of aggregation of the particulate matter may also be an amount of particulate matter which has released the electrons. Moreover, it may also be an amount of decrease in the number of particles of the particulate matter.

However, when HC, CO, or the like, which is unburnt fuel, is contained in the exhaust gas, the unburnt fuel serves as a carrier, so when a voltage is applied to the electrode, an electric current passes to it through the unburnt fuel, etc. This electric current is detected in the current detection device. Then, in cases where the air fuel ratio of the exhaust gas is a rich air fuel ratio, a lot of unburnt fuel is contained in the exhaust gas, so the electric current detected by the current detection device becomes very large.

That is, in cases where the air fuel ratio of the exhaust gas is a rich air fuel ratio, the electric current detected by the current detection device becomes larger, and hence, it becomes difficult to estimate the amount of aggregation of the particulate matter. Accordingly, in cases where the air fuel ratio of the exhaust gas is a rich air fuel ratio, an estimation by the estimation device is prohibited. As a result of this, it is possible to suppress the reduction or decrease in the estimation accuracy of the amount of aggregation of the particulate matter. Accordingly, for example, it is possible to achieve to make the voltage applied to the electrode suitable.

In the present invention, provision is made for:
an insulation part that insulates electricity between said processing part and said exhaust passage; and
a ground part that grounds said processing part;
wherein said current detection device can detect the electric current in said ground part.

Here, note that the current detection device detects the electric current at an electric potential reference point side from the electrode. In general, wiring is often longer or thicker at a power supply side from the electrode than at a ground side from the electrode. In addition, electric charges may be stored at the power supply side from the electrode. Then, in cases where an electric current is detected in the power supply side from the electrode, even if a strong discharge is generated in the electrode, the rising and falling of the electric current detected by the current detection device at that time become slow. On the other hand, in the ground side from the electrode, wiring can be made relatively short and thin. For this reason, it is possible to detect the electric current in a more accurate manner. Also, due to the provision of the insulation part, it is possible to suppress electricity from flowing to other than the ground part. As a result of this, it is possible to detect the electric current in a further accurate manner.

Moreover, in the present invention, said estimation device can make an estimation that the larger the electric current detected by said current detection device, the larger the amount of aggregation of the particulate matter is.

Because the amount of aggregation of the particulate matter has a correlation with the detected electric current, an estimation can be made that the larger the electric current to be detected, the more the amount of aggregation of the particulate matter is. However, when the air fuel ratio of the exhaust gas becomes a rich air fuel ratio, the electric current will become larger due to the influence of unburnt fuel. In this case, in spite of the fact that the amount of aggregation of the particulate matter is small, there is a fear that it may be estimated that the amount of aggregation of the particulate matter is large. In contrast to this, in cases where the air fuel ratio is rich, by prohibiting the estimation by the estimation device, it is possible to enhance the estimation accuracy.

Effect of the Invention

According to the present invention, the amount of aggregation of particulate matter can be estimated with a high degree of accuracy.

MODE FOR CARRYING OUT THE INVENTION

Hereinafter, reference will be made to a specific embodiment of a particulate matter processing apparatus according to the present invention based on the attached drawings.

First Embodiment

Figure 1:
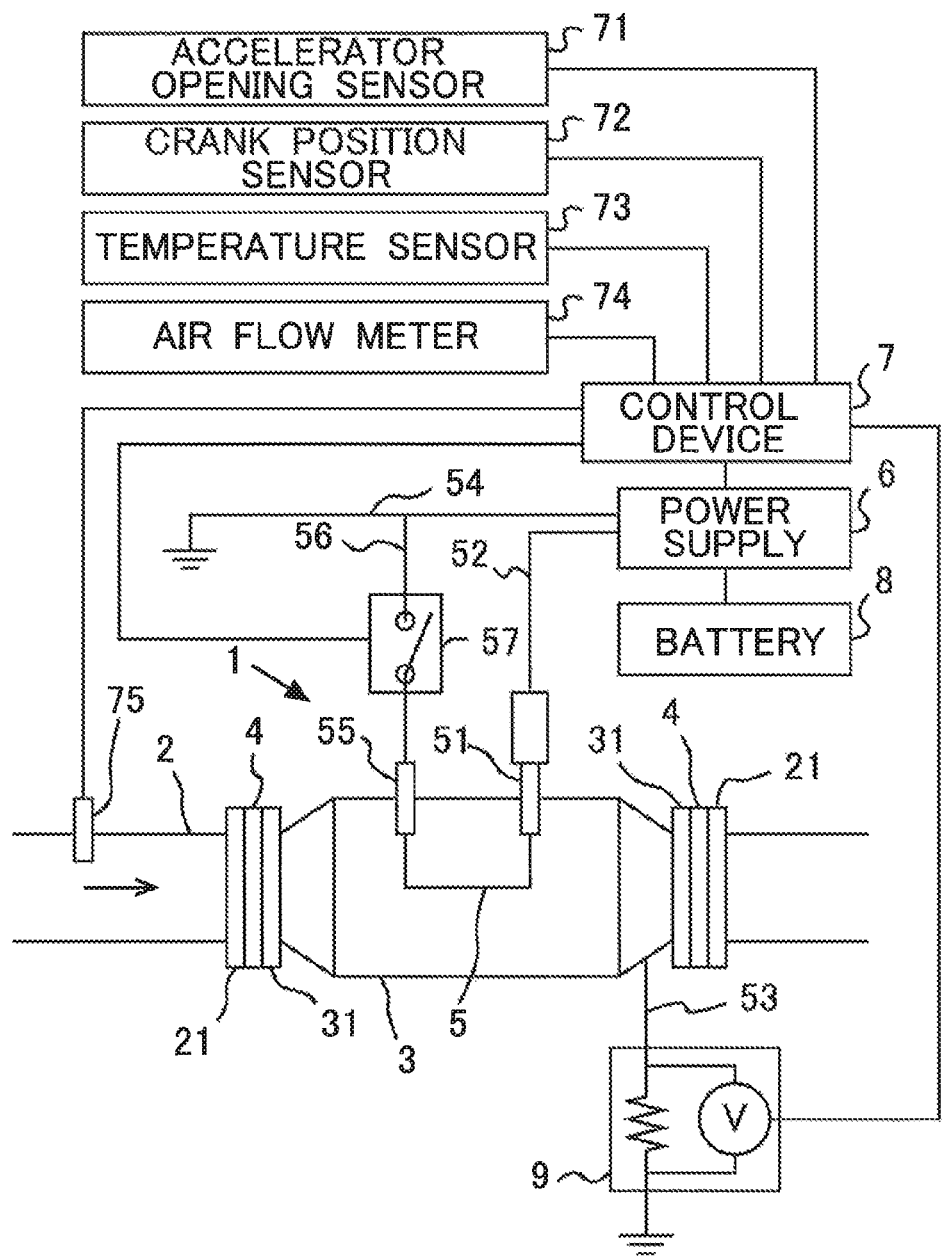
FIG. 1 is a view showing the schematic construction of a particulate matter processing apparatus according to ant embodiment of the present invention.

FIG. 1 is a view showing the schematic construction of a particulate matter processing apparatus 1 according to this embodiment of the present invention. The particulate matter processing apparatus 1 is arranged in an exhaust passage 2 of a gasoline engine of a spark ignition type.

The particulate matter processing apparatus 1 is constructed to include a housing 3 which is connected at its opposite ends with the exhaust passage 2. As a material for the housing 3, there is used a stainless steel material. The housing 3 is formed into a hollow cylindrical shape with its diameter being larger than that of the exhaust passage 2. The opposite end portions of the housing 3 are each formed into a tapered shape of which the cross-sectional area becomes smaller as they become closer to their end. Here, note that in FIG. 1, an exhaust gas flows through the exhaust passage 2 in the direction of an arrow, and flows into the interior of the housing 3. For this reason, the housing 3 may also be a part of the exhaust passage 2.

The exhaust passage 2 and the housing 3 are connected to each other through a pair of insulation parts 4. The insulation parts 4 are each made of an electrically insulating material. The insulation parts 4 are each sandwiched between a flange 21, which is formed at an end of the exhaust passage 2, and a flange 31, which is formed at one adjacent end of the housing 3. The exhaust passage 2 and the housing 3 are fastened to each other, for example, by means of bolts and nuts. Then, these bolts and nuts are also subjected to insulation processing so as to prevent electricity from flowing through these bolts and nuts. In this manner, electricity is prevented from flowing between the exhaust passage 2 and the housing 3.

An electrode 5 is mounted on the housing 3. The electrode 5 penetrates through a side surface of the housing 3, extends from the side surface of the housing 3 in the direction of a central axis thereof, then bends to an upstream side of the flow of the exhaust gas in the vicinity of the central axis, and extends again toward the upstream side of the flow of the exhaust gas in parallel to the central axis. Then, the electrode 5 further bends to a side surface side of the housing 3 at its upstream side, and leads to the outside while penetrating through the side surface of the housing 3.

In addition, the electrode 5 is provided with insulator parts 51, 55 made of an electrically insulating material, which serve to prevent electricity from flowing between the electrode 5 and the housing 3. These insulator parts 51, 55 are located between the electrode 5 and the housing 3, and have each a function of insulating electricity and at the same time fixedly securing the electrode 5 to the housing 3.

Then, the electrode 5 has its one end connected to a power supply 6 through a power supply side electric wire 52. The power supply 6 can supply electricity to the electrode 5 and at the same time change a voltage to be applied thereto. This power supply 6 is connected to a control device 7 and a battery 8 through an electric wire. The control device 7 controls the voltage which is applied to the electrode 5 by the power supply 6. In addition, a ground electric wire 54 for connecting the power supply 6 to a reference point of electric potential is connected to the power supply 6. The power supply 6 is connected to ground through this ground electric wire 54.

Moreover, the electrode 5 has its other end connected to the ground electric wire 54 through a short circuit electric wire 56. To the middle of the short circuit electric wire 56, a switch 57 for opening and closing an electric circuit is provided or connected. An electric current flows through the short circuit electric wire 56 by turning the switch 57 into an ON state during the application of a voltage by the power supply 6. At this time, the electrode 5 is placed in a short-circuited state, so the temperature of the electrode 5 goes up. Here, note that in this embodiment, the power supply side electric wire 52 is connected to the downstream side insulator part 51 and the short circuit electric wire 56 is connected to the upstream side insulator part 55, but instead of this, the short circuit electric wire 56 may be connected to the downstream side insulator part 51, and the power supply side electric wire 52 may be connected to the upstream side insulator part 55.

Also, a ground side electric wire 53 is connected to the housing 3, so that the housing 3 is connected to ground through the ground side electric wire 53. A detection device 9, which serves to detect the electric current passing through the ground side electric wire 53, is provided or connected to the ground side electric wire 53. The detection device 9 detects the electric current, for example, by measuring a potential difference between opposite ends of a resistance which is provided or inserted in the middle of the ground side electric wire 53. This detection device 9 is connected to the control device 7 through an electric wire. Then, the electric current detected by the detection device 9 is inputted to the control device 7. Here, note that, the ground side electric wire 53 is smaller in electric capacity than the power supply side electric wire 52, so a response at the time of detecting an electric current is higher when the detection device 9 is provided or connected to the ground side electric wire 53 than when the detection device 9 is provided or connected to the power supply side electric wire 52. Also, note that in this embodiment, the detection device 9 corresponds to a current detection device in the present invention.

In addition, an accelerator opening sensor 71, a crank position sensor 72, a temperature sensor 73, an air flow meter 74, and an air fuel ratio sensor 75 are connected to the control device 7. The accelerator opening sensor 71 detects an engine load by outputting an electric signal corresponding to an amount of depression of an accelerator pedal at which the driver of a vehicle with the internal combustion engine installed thereon has depressed or stepped down the accelerator pedal. The crank position sensor 72 detects the number of engine revolutions per unit time. The temperature sensor 73 detects the temperature of the internal combustion engine by detecting the temperature of cooling water or the temperature of lubricating oil in the internal combustion engine. The air flow meter 74 detects an amount of intake air sucked into the internal combustion engine. The air fuel ratio sensor 75 is mounted on the exhaust passage 2 at a location upstream of the housing 3, and detects the air fuel ratio of the exhaust gas which flows through the exhaust passage 2. Here, note that in this embodiment, the air fuel ratio sensor 75 corresponds to an air fuel ratio detection device in the present invention. In addition, the air fuel ratio of the exhaust gas may be estimated from an operating state of the internal combustion engine.

Moreover, the switch 57 is connected to the control device 7 through an electric wire, so that the control device 7 performs an ON-OFF operation of the switch 57. Here, by turning the switch into the ON state during the time when a voltage is applied to the electrode 5 from the power supply 6, an electric current passes through the short circuit electric wire 56. On the other hand, by turning the switch into an OFF state, the electric current passing through the short circuit electric wire 56 is put into a stopped state.

In the particulate matter processing apparatus 1 as constructed in this manner, electrons are released from this the electrode 5 by applying a negative direct current voltage from the power supply 6 to the electrode 5 when the switch 57 is in the OFF state. That is, electrons are caused to be released from the electrode 5 by making the electric potential of the electrode 5 lower than that of the housing 3. Then, particulate matter in the exhaust gas can be charged to negative polarity by means of these electrons. The particulate matter thus charged to negative polarity is caused to move by means of a Coulomb force and a gas stream of the exhaust gas. Thereafter, when the particulate matter reaches the housing 3, the electrons, which have charged the particulate matter to negative polarity, will be released to the housing 3. The particulate matter, which has released the electrons to the housing 3, aggregates, thereby making larger the particle diameter or size of each particle. In addition, the number of particles in the particulate matter is reduced due to the aggregation of particulate matter. That is, by applying the voltage to the electrode 5, the diameters or sizes of particles in the particulate matter can be made larger, thus making it possible to reduce the number of particles in the particulate matter.

Then, assuming that the amount of decrease in the number of particles in the particulate matter is the amount of aggregation of the particulate matter, the amount of aggregation of the particulate matter has a correlation with the number of electrons which have been released from the particulate matter to the housing 3. Accordingly, if the relation between the detected electric current and the amount of aggregation of particulate matter has beforehand been obtained through experiments, etc., it will be possible to estimate the amount of aggregation of the particulate matter based on the detected electric current. Here, note that it is estimated that the larger the detected electric current, the more the amount of aggregation of the particulate matter is. Then, by estimating the amount of aggregation of the particulate matter, a determination can be made as to whether the voltage to be applied is suitable. In addition, the voltage to be applied can be controlled based on the amount of aggregation of the particulate matter.

Incidentally, if unburnt fuel such as HC, CO, etc., is contained in the exhaust gas, upon application of a voltage to the electrode 5, the unburnt fuel will serve as a carrier for electrons, so that an ionic current will flow. Then, when the air fuel ratio of the exhaust gas becomes a rich air fuel ratio, the amount of the unburnt fuel in the exhaust gas will increase, and the ionic current will increase, as a result of which the electric current to be detected will become larger.

Then, if the amount of aggregation of the particulate matter is estimated at the time when the air fuel ratio of the exhaust gas is a rich air fuel ratio, there will be a fear that the estimation accuracy of the amount of aggregation of the particulate matter may become lower. That is, there will be a fear that when the detected electric current is increased due to an increase in the unburnt fuel, it may be estimated that the amount of aggregation of the particulate matter has increased. However, in cases where the amount of aggregation of the particulate matter is estimated based on the detected electric current, it is difficult to distinguish between whether the electric current flows due to an aggregation of the particulate matter or whether the detected electric current increases due to an increase in the unburnt fuel.

Accordingly, in this embodiment, in cases where the air fuel ratio of the exhaust gas is a rich air fuel ratio, the estimation of the amount of aggregation of the particulate matter is prohibited. Here, note that the control based on the amount of aggregation of the particulate matter may be prohibited.

Here, note that in this embodiment, due to the provision of the insulation parts 4, it is suppressed that electricity passes to the exhaust passage 2. Accordingly, the electric current, which passes to the housing 3 through deposits on the electrode 5, the particulate matter afloat in the exhaust gas, and the unburnt fuel, is detected by the detection device 9. In addition, the detection accuracy of electric current can be enhanced by detecting the electric current in the ground side electric wire 53. In general, the power supply side electric wire 52 is often longer in wiring length or thicker in wiring diameter than the ground side electric wire 53. Then, if an electric current is detected in the power supply side electric wire 52, the rising and falling of the detected electric current become slower than the actual change of electric current. For this reason, there is a fear that the detection accuracy of the electric current may become low.

On the other hand, in the ground side electric wire 53, wiring can be made relatively short and thin. For this reason, the response to an actual change of electric current is higher when the electric current is detected in the ground side electric wire 53. Accordingly, by detecting the electric current in the ground side electric wire 53, it is possible to detect the electric current in a more accurate manner.

Figure 2:
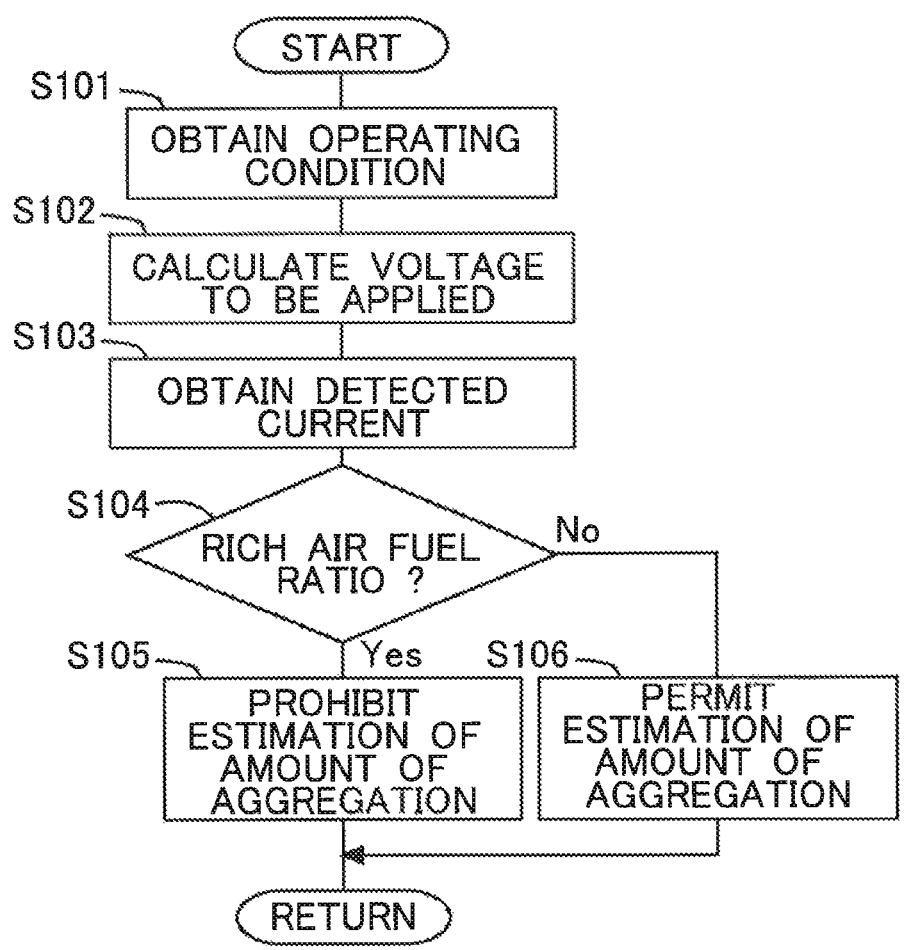
FIG. 2 is a flow chart showing a flow for estimating an amount of aggregation of particulate matter according to the embodiment.

Next, FIG. 2 is a flow chart showing a flow (routine) for estimating the amount of aggregation of the particulate matter according to this embodiment. This routine is carried out by means of the control device 7 in a repeated manner at each predetermined time interval.

In step S101, the operating state of the internal combustion engine is obtained. For example, the values to be needed for hereafter processing, such as the number of engine revolutions per unit time, the engine load, the air fuel ratio of the exhaust gas, and so on, are read in. The number of engine revolutions per unit time is detected by the crank position sensor 72, and the engine load is detected by the accelerator opening sensor 71. In addition, the air fuel ratio of the exhaust gas is detected by the air fuel ratio sensor 75. Here, note that the air fuel ratio of the exhaust gas can also be estimated from the number of engine revolutions per unit time, the engine load, the temperature of the internal combustion engine, and so on. Also, the temperature of the internal combustion engine (e.g., the temperature of lubricating oil or the temperature of cooling water) is detected by the temperature sensor 73.

In step S102, the voltage to be applied to the electrode 5 is calculated. The voltage to be applied is set according to the number of particles in the particulate matter (pieces/cm$^3$) estimated. This number of particles in the particulate matter is the number of particles in the particulate matter which are emitted by the internal combustion engine, and is the number of particles in the particulate matter before the particulate matter flows into the housing 3. The number of particles in the particulate matter has a correlation with the number of engine revolutions per unit time, the engine load, and the temperature of the internal combustion engine (e.g., the temperature of the lubricating oil or temperature of cooling water), and hence is calculated based on these values. A plurality of maps according to the temperature of the internal combustion engine may be stored which are used for calculating the number of particles in the particulate matter from the number of engine revolutions per unit time and the engine load, and the number of particles in the particulate matter may be calculated based on these maps.

Here, note that a sensor for detecting the number of particles in the particulate matter may be mounted on the exhaust passage 2 at a location upstream of the housing 3, so that the number of particles in the particulate matter is detected by this sensor.

Then, the voltage to be applied is calculated based on the number of particles in the particulate matter and the amount of exhaust gas (g/sec) in the internal combustion engine. Such a relation may have beforehand been obtained through experiments, etc., and made into a map. The amount of exhaust gas in the internal combustion engine has a correlation with the amount of intake air in the internal combustion engine, and hence, can be obtained based on the amount of intake air detected by the air flow meter 74.

Here, the smaller the amount of exhaust gas, the smaller becomes the inertia force of the particulate matter, and hence, the influence of an electrostatic action becomes relatively larger. For this reason, it becomes easy for the particulate matter to aggregate. Accordingly, the smaller the amount of exhaust gas, with the smaller voltage to be applied, the particulate matter aggregates. As a result, the smaller the amount of exhaust gas, the smaller the voltage to be applied is made. In addition, the more the number of particles in the particulate matter, the shorter become the distances between adjacent particles in the particulate matter, and hence, the influence of the electrostatic action becomes relatively larger. For this reason, the more the number of particles in the particulate matter, with the smaller voltage to be applied, the particulate matter aggregates. As a result, the more the number of particles in the particulate matter, the smaller the voltage to be applied is made.

In addition, the voltage to be applied may also be, for example, be such a value that the reduction or decrease rate of the number of particles in the particulate matter becomes a predetermined value (e.g., 40%). Also, the voltage to be applied may also be a specified value which has been set beforehand.

Then, after the voltage to be applied is calculated, this voltage is applied, and the routine goes to step S103, in which an electric current is detected. This electric current is a value detected by the detection device 9.

In step S104, it is determined whether the air fuel ratio of the exhaust gas obtained in step S101 is a rich air fuel ratio. In this step, it is determined whether a lot of unburnt fuel is contained in the exhaust gas.

Then, in cases where an affirmative determination is made in step S104, the routine goes to step S105, whereas in cases where a negative determination is made, the routine goes to step S106.

In step S105, the estimation of the amount of aggregation of the particulate matter is prohibited. That is, an accurate determination can not be carried out under the influence of unburnt fuel, so the estimation is prohibited. Here, note that in this embodiment, the control device 7, which carries out the processing of step S105, corresponds to a prohibition device in the present invention.

On the other hand, in step S106, the estimation of the amount of aggregation of the particulate matter is permitted. Then, the estimation of the amount of aggregation of the particulate matter is made based on the detected electric current, and the control of the voltage to be applied is carried out as necessary. Here, note that in this embodiment, the control device 7, which carries out the processing of step S106, corresponds to an estimation device in the present invention.

In this manner, the estimation of the amount of aggregation of the particulate matter is prohibited at the time of a rich air fuel ratio, so it is possible suppress the reduction or decrease in the estimation accuracy of the amount of aggregation of the particulate matter. As a result of this, it is possible to carry out control based on the amount of aggregation of the particulate matter in a suitable manner.

EXPLANATION OF REFERENCE NUMERALS AND CHARACTERS 1 particulate matter processing apparatus
2 exhaust passage
3 housing
4 insulation parts
5 electrode
6 power supply
7 control device
8 battery
9 detection device
21 flange
31 flange
51 insulator part
52 power supply side electric wire
53 ground side electric wire
54 ground electric wire
55 insulator part
56 short circuit electric wire
57 switch
71 accelerator opening sensor
72 crank position sensor
73 temperature sensor
74 air flow meter
75 air fuel ratio sensor

The invention claimed is:

1. A particulate matter processing apparatus comprising:
a housing that has a space inside thereof and that is provided in an exhaust passage of an internal combustion engine;
an electrode installed in the space inside of said housing;
a power supply that is connected to said electrode and applies a voltage thereto;
a control unit that charges particulate matter between said housing and said electrode by generating a potential difference between said housing and said electrode by said power supply, and that aggregates the particulate matter by releasing electrons from the particulate matter in said housing;
a current detection device that detects an electric current which flows due to release of electrons from the particulate matter in said housing at the time when the voltage is applied to said electrode by said power supply;
an estimation device that estimates an amount of aggregation of the particulate matter based on the electric current detected by said current detection device at the time when the voltage is applied to said electrode by means of said power supply;
an air fuel ratio detection device that detects or estimates an air fuel ratio of an exhaust gas which flows through said exhaust passage; and
a prohibition device that prohibits the estimation by said estimation device in cases where the air fuel ratio detected or estimated by said air fuel ratio detection device is a rich air fuel ratio.

2. The particulate matter processing apparatus as set forth in claim 1, further comprising:
an insulation part that insulates electricity between said housing and said exhaust passage; and
a ground part that grounds said housing;
wherein said current detection device detects the electric current in said ground part.

3. The particulate matter processing apparatus as set forth in claim 1, wherein
said estimation device makes an estimation that the larger the electric current detected by said current detection device, the larger the amount of aggregation of the particulate matter is.

4. The particulate matter processing apparatus as set forth in claim 2, wherein
said estimation device makes an estimation that the larger the electric current detected by said current detection device, the larger the amount of aggregation of the particulate matter is.

* * * * *